US004001639B2

United States Statutory Invention Registration [19]

[11] Reg. Number: H1639

[45] Published: Mar. 4, 1997

Crainic

[54] CATAMENIAL DEVICE

[76] Inventor: Sorin Crainic, Sulzbacher Strasse 40-50, 65824 Schwalbach am Taunus, Germany

[21] Appl. No.: 335,746

[22] PCT Filed: May 11, 1993

[86] PCT No.: PCT/US93/04525

§ 371 Date: Mar. 16, 1995

§ 102(e) Date: Mar. 16, 1995

[87] PCT Pub. No.: WO93/22998

PCT Pub. Date: Dec. 25, 1993

[30] Foreign Application Priority Data

May 15, 1992 [EP] European Pat. Off. ..... 92201394

[51] Int. Cl.[6] ..... A61F 13/15

[52] U.S. Cl. ..... 604/368; 604/358

[58] Field of Search ..... 604/358, 365, 604/368, 372, 378, 385.1

[56] References Cited

U.S. PATENT DOCUMENTS

| | | | |
|---|---|---|---|
| 4,055,180 | 10/1977 | Karami | 604/378 |
| 5,002,814 | 3/1991 | Knack et al. | 604/385.1 |
| 5,061,259 | 10/1991 | Goldman et al. | 604/368 |
| 5,180,622 | 1/1993 | Berg et al. . | |
| 5,300,565 | 4/1994 | Berg et al. . | |
| 5,330,822 | 7/1994 | Berg et al. . | |
| 5,342,334 | 8/1994 | Thompson et al. | 604/370 |

FOREIGN PATENT DOCUMENTS

| | | | |
|---|---|---|---|
| 2266464 | 11/1993 | United Kingdom | 604/378 |
| WO87/00848 | 2/1987 | WIPO . | |

*Primary Examiner*—Charles T. Jordan
*Assistant Examiner*—Meena Chelliah

[57] ABSTRACT

A catamenial device comprises a fluid permeable, body facing, topsheet (25), a liquid impermeable barrier layer and an absorbent body (34) disposed between the topsheet (25) and the barrier layer, the absorbent body (34) incorporating a water insoluble particular hydrogel material at a loading of at least 40 g/m$^2$ of the plan area of the absorbent body, the water insoluble particulate hydrogel material having a gel strength of at least 0.38 kPa after 5 minutes exposure to synthetic urine solution in the modified AGE P test, a device incorporating insoluble particulate hydrogel material absorbing at least 40 g sheep's blood in the Total Capacity Storage Test.

1 Claim, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CATAMENIAL DEVICE

This invention relates to disposable catamenial devices. More particularly it relates to disposable sanitary napkins and pantiliners designed to be located externally of the vaginal cavity and to be held in position adjacent the vaginal opening by the wearer's undergarment.

A major design objective of catamenial devices of this type is that they be non bulky whilst providing adequate menses absorption capability in order to be comfortable and non-obtrusive as well as effective in use.

The use of water insoluble particulate hydrogel material as an absorbent material in disposable absorbent articles such as disposable diapers, incontinence briefs and catamenial devices has permitted significant reductions to be made in the bulk of such articles without a sacrifice in absorbent capacity. Within the field of catamenial devices, a category of thin flexible sanitary napkin products has been developed and introduced commercially that takes advantage of the high absorbency of particulate hydrogel material. The commonly assigned EP-A-0336578 discloses a sanitary, napkin of this general type.

Nevertheless, in spite of the commercial introduction of catamenial devices incorporating particulate hydrogel material as the, or the major component of the, absorbent medium, there remains a perception amongst users that thin sanitary napkins are only suitable for light or low menstrual flows or as pantiliners. Attempts to change this perception by increasing the level of hydrogel material in the structure have proved ineffective as such increases in level have resulted in a pronounced 'gel blocking'effect with a loss in efficiency of usage of the hydrogel material and, under certain conditions, adverse effects on overall absorbent capacity.

When a hydrogel material absorbs aqueous liquids and swells, the ability of the resultant gel to maintain its integrity, particularly under pressure correlates with the 'gel strength' of the material. 'Gel strength' is a composite of several properties, but for the purposes of the present invention can be expressed in terms of the modified Absorbent Gel Expansion Pressure test (hereinafter referred to as the modified AGEP test). References hereinafter to gel strength values are to the values obtained in this test.

The particulate hydrogel materials used in current commercially available disposable absorbent products have been developed primarily for disposable diapers in which the major load is urine. Whilst such hydrogel materials provide a satisfactory balance between absorbency and other properties such as gel strength when exposed to liquids that are almost entirely aqueous, they appear not to be optimum for more complex liquid materials such as menses. Accordingly a need has been identified for a particulate hydrogel material that is menses specific i.e. has the capability of absorbing blood and protein-containing liquids without gel blocking.

The Applicant has now surprisingly found that certain types of hydrogel material which have high gel strength but relatively low absorbent capacity and which also retain, or more preferably increase, their gel strength after absorbing a liquid load, provide enhanced performance in catamenial devices. This gel strength behaviour, when the hydrogel is subjected to a liquid load, minimises the gel blocking effect and permits the majority, if not all of the absorbent capacity to be utilised.

According to the present invention there is provided a catamenial device comprising a liquid permeable layer having a first body-facing surface and a second opposed surface, an absorbent body disposed adjacent the opposed surface said absorbent body comprising a water insoluble particulate hydrogel material at a weight concentration of at least 5 g/m$^2$ of the plan area of the absorbent body, a liquid impermeable barrier layer disposed on the surface of said absorbent body remote from said liquid permeable layer, and adhesive attachment means for securing said device to a garment, said attachment means being disposed on the surface of said device opposed to said first body facing surface of said liquid permeable layer, wherein the water insoluble particulate hydrogel material has a gel strength of at least 0.38 kPa after 5 minutes and not less than 0.38 kPa after 30 minutes exposure to a synthetic urine solution in a modified AGEP test and in that said device incorporating 0.8 g water insoluble particulate hydrogel material absorbs at least 40 g sheeps blood in the Total Storage Capacity Test.

Preferably the gel strength of the hydrogel after 5 minutes is greater than 0.48 kPa and more preferably is greater than 0.54 kPa. Preferably also the gel strength of the hydrogel after 30 minutes increases generally uniformly to a value greater by at least 25% of its value after 5 minutes and more preferably to a value greater by at least 50%. Most preferably the gel strength after 30 minutes is greater by at least 75% of its value after 5 minutes.

In its broadest aspect the sanitary napkin structure comprises a fluid permeable layer, a fluid impermeable barrier layer and an absorbent means, comprising a water insoluble particulate hydrogel material as defined above, disposed therebetween. The fluid permeable layer can constitute a single sheet of woven or non woven fibers which may be of natural or synthetic origin or a perforated film of polymeric material. Alternatively the fluid permeable layer can itself comprise a composite of several sheets of the same or different materials, each of which has a distinct function. The fluid impermeable barrier layer is conventionally a film of polymeric plastics material but may itself form part of a composite in which sheets of other materials may be components. The absorbent means may comprise the water insoluble particulate hydrogel material on its own, but is more commonly a composite structure in which the hydrogel material is held between or enveloped in a web or webs of fluid permeable fibrous material, or mixed with such fibrous material to form an absorbent web.

In one preferred embodiment, the sanitary napkin comprises, from the body surface down, an apertured formed film topsheet, an apertured nonwoven wipe acquisition sheet, a wet-laid tissue, the superabsorbent core, and a barrier sheet. In a preferred embodiment, the napkin also has laterally extending laps which drape over the edges of the wearer's panties in the crotch and are attachable to the garment side of the wearer's panties.

BRIEF DESCRIPTION OF THE DRAWINGS

The invention is illustrated in the drawings in which.

DETAILED DESCRIPTION OF PREFERRED EMBODIMENTS

The present invention relates to female sanitary napkins and in particular to sanitary napkins which are thin and flexible and offer enhanced fit, comfort, and containment.

As used herein, the term "sanitary napkin" refers to an article which is worn by females adjacent to the pudendal region and which is intended to absorb and contain the various exudates which are discharged from the body (e.g. blood, menses and urine) and which is intended to be discarded after a single use (i.e. it is not intended to be laundered or otherwise restored or reused). Interlabial devices which reside partially within and partially external of the wearer's vestibule are also within the scope of this invention. As used herein, the term "pudendal" refers to the externally visible female genitalia and is limited to the labia majora, the labia minora, the clitoris, and the vestibule.

Figure 1:
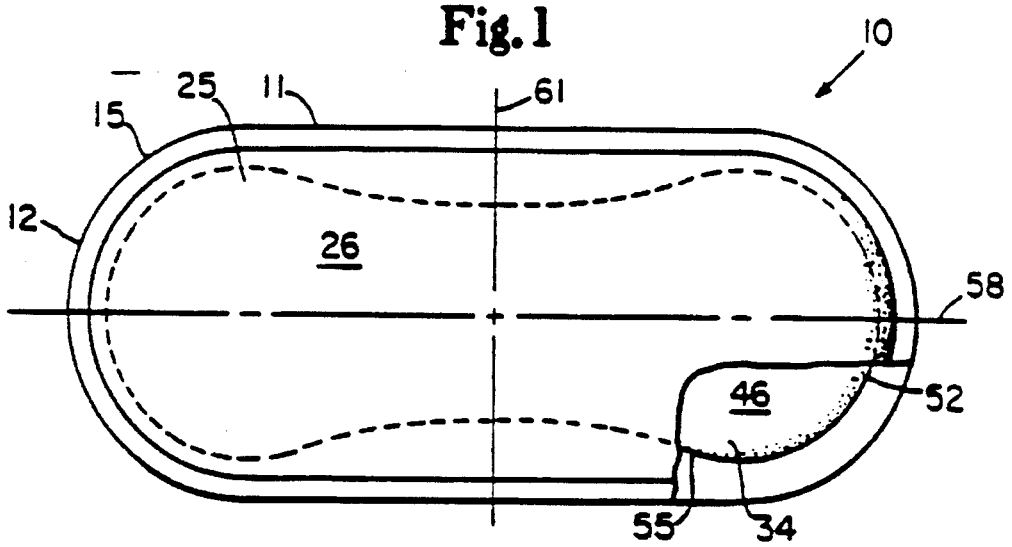
FIG. 1 is a top plan view of a preferred sanitary napkin embodiment of the present invention with portions being torn away to show underlying structure.
Figure 2:
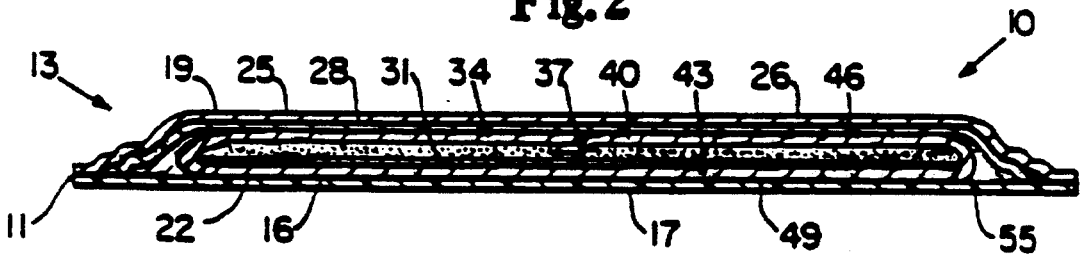
FIG. 2 is a lateral cross-sectional view of the preferred sanitary napkin embodiment shown in FIG. 1 taken along line 2—2 of FIG. 1.

A preferred embodiment of a sanitary napkin 10 of the present invention is shown in FIGS. 1 and 2. As can be seen in FIGS. 1 and 2, a preferred sanitary napkin 10 basically comprises an absorbent means 13 and a liquid impermeable barrier layer 16. The absorbent means 13 comprises a water-insoluble particulate hydrogel material of defined characteristics but otherwise may be any means which is generally compressible, conformable and non-irritating to the wearer's skin and which is capable of absorbing and containing body exudates such as menses, blood and urine. Preferably, the absorbent means 13 maintains integrity, when wetted, in use. The absorbent means 13 has a first surface 19 and a second major surface 22. The barrier layer 16 is adjacent the second major surface 22 of the absorbent means 13. The barrier layer 16 may be any means which is flexible and liquid impervious and which prevents the exudates absorbed and contained in the absorbent means 13 from wetting articles such as panties which contact the sanitary napkin 10.

In the preferred embodiment shown in FIGS. 1 and 2, the absorbent means 13 comprises a liquid permeable layer comprising topsheet 25 together with a wipe acquisition sheet 28 in combination with absorbent body 34. In the preferred embodiment shown in FIGS. 1 and 2, the barrier means 16 is a barrier sheet, the absorbent body 34 is comprised of hydrogel-forming material 37 disposed between two layers of air-laid tissue 40 and 43. The first and second tissue layers 40 and 43 provide containment of the hydrogel-forming polymeric gelling agent 37, improve lateral wicking of the absorbed exudates throughout the absorbent body 34 and provide a degree of absorbency. The sanitary napkin 10 has side edges 11 and end edges 12 which together form the periphery 15 of the sanitary napkin 10. The sanitary napkin 10 has a body surface 26 which is generally defined by the topsheet 25, and a garment surface 17 which is generally defined by the barrier sheet 16.

The total absorbent capacity of the absorbent body 34 should be compatible with the design exudate loading for the intended use of the sanitary napkin 10. Further, the absorbent capacity of the absorbent body 34 may be varied to accommodate wearers ranging in the expected amount of exudate fluid volume. For instance, a different absorbent capacity may be utilized for sanitary napkin intended for daytime use as compared with those intended for night-time use, or for sanitary napkin intended for use by teenage females as compared with those intended for use by more mature women. The absorbent body 34 may be manufactured in a wide variety of shapes (e.g. rectangular, hourglass, etc.). A preferred shape of the absorbent body 34 is the dogbone shape shown in FIG. 1, typically having a longitudinal dimension along the longitudinal centerline 58 of 22.0 cm., a lateral dimension along the lateral centerline 61 of 7.0 cms and a lateral dimension of 8.0 centimeters across its widest portion. Preferably, the central width of the absorbent is at least 7.0 centimeters and the caliper of the napkin as a whole is less than 3.0 millimeters more preferably less than 2.5 millimeters.

In a preferred embodiment, the sanitary napkin 10 of the present invention will have a hydrogel-forming polymeric gelling agent distributed over at least 100 $cm^2$ of the plan area of the absorbent body, more preferably over an area of at least 125 $cm^2$, even more preferably over an area of at least 150 $cm^2$, and most preferably over the entire plan area of the absorbent body 34. The hydrogel-forming polymeric gelling agent will be present in an amount of at least 0.0005 $g/cm^2$ up to about 0.009 $g/cm^2$. Higher amounts per unit area can be used but show a correspondingly less increased benefit. More usually a loading of at least 0.002 $g/cm^2$ is employed, preferably at least 0.004 $g/cm^2$ and more preferably the loading lies in the range of from 0.0045 $g/cm^2$ to 0.008 $g/cm^2$. Most preferably the amount of gelling material per unit area lies in the range from 0.005 $g/cm^2$ to 0.007 $g/cm^2$. Preferably, the absorbent body 34 will contain from 5.0% to 85.0% by weight of hydrogel-forming polymeric gelling agent, more preferably from 10.0% to 70.0%, and most preferably from 15.0% to 55.0%. In practice this corresponds to a weight of from 0.6 g to 1.5 g or more preferably of a weight from 0.7 g to 1.25 g and most preferably of a weight from 0.75 g to 1.0 g of polymeric gelling agent in the napkin.

In the illustrated embodiment, the absorbent body 34 is symmetrically configured for ease of manufacture and so that no conscious effort is required by the wearer to properly place the napkin 10 in the direction it should be worn. However, the present invention is not limited to symmetrical structures and the basic requirement is merely that the midportion is shaped to conform to the wearer's thighs and to the edges of the thinner crotch portion of the wearer's panties so as to prevent excessive bunching.

Referring to FIG. 2, the absorbent body 34 has a first major surface 46, a second major surface 49, a pair of end edges 52 and a pair of side edges 55. The absorbent body 34 may also be attached over its first or second major surfaces 46 and 49, respectively, to adjacent members such as the topsheet 25 and barrier sheet 16 by any of the means well known in the art, such as by spray-glueing by spiral glueing or by lines or spots of adhesive. Such attachment provides integrity and facilitates recoverability of the absorbent materials in use so as to maintain an optimum degree of absorbency. Preferably, the absorbent body 34 has a wet-tensile strength in the cross-direction of at least 1 Newton per centimeter. Wet tensile strength is determinable by ASTM Standard D 829-49.

In the preferred embodiment shown in FIG. 2, the absorbent body 34 is a laminate comprised of a layer of superabsorbent polymer material 37 disposed between two layers of air laid tissue 40 and 43. This laminate is preferably formed as follows. A continuous web of air laid cellulosic tissue 43 of slightly more than twice the desired width of the absorbent body is provided with a band of adhesive 31 on its upper surface, the adhesive band having a width slightly less than the width of the tissue 43. A suitable adhesive is a hot melt adhesive such as HL 1222 supplied by H.B. Fuller GmbH, An der Roten, Bleiche, D-21210 Luneberg, Germany. Superabsorbent polymeric gelling material is then fed to the web so as to form a layer 37 of the desired weight per unit area having a width corresponding to the desired width of the absorbent body. The layer 37 of polymeric gelling material is thus held in position by the adhesive 31 on the tissue web 43 and does not migrate or sift through the absorbent pad.

The side edge portions of the tissue web 43 are then folded inwardly over the adhered layer of polymeric gelling material 37 so as to form the upper tissue layer 40, and to adhere the side edge portions to an upper surface of the layer 37 of polymeric gelling material. The longitudinal edges of the side edge portions preferably overlap in the region of the longitudinal centre line of the web. The folded laminate is then severed into portions of the desired length to form individual absorbent cores. The cutter used to sever the individual portions is shaped so that the ends of the core are rounded. In the preferred embodiment shown in FIGS. 1 and 2, the cutter is shaped to follow the circumference of a circle of radius approximately 38 mm.

In the embodiment of FIG. 2, the tissue layer 40 of absorbent body 34 forms the upper tissue layer of the laminate in the assembled napkin, such that the overlapped tissue side edge portions are disposed adjacent the wipe acquisition sheet. In an alternative embodiment the absorbent body 34 may be inverted during manufacture so that the layer 43 is disposed uppermost in the assembled napkin.

The primary absorbent material forming the core of the absorbent body is a water insoluble particulate gelling agent capable of forming a hydrogel when it absorbs aqueous liquids. In this connection, particulate includes granules, flakes, rods, fibers, cubes, spheres and agglomerates of finer particles.

Aqueous liquids, such as urine and body fluids, discharged into the absorbent body 34 can be acquired and held by the polymeric gelling agent, thereby providing the articles herein with enhanced absorbent capacity, and/or improved fluid retention performance. In principle, any material capable of forming a stable water-insoluble gel on absorption of aqueous liquid can be used as the particulate gelling agent. Suitable materials of this type include chain entangled high molecular polymers cellulose derivatives such as carboxymethylcellulose, hydrophilic polymers grafted onto cellulose or starch backbones and cross linked co-polymeric materials based on acrylic acid.

The polymeric gelling agent which is employed in the case of the absorbent body 34 will preferably comprise particles of a substantially water-insoluble, slightly cross-linked, partially neutralized, hydrogel-forming polymer material. Such polymer materials can be prepared from polymerizable, unsaturated, acid-containing monomers. Suitable unsaturated acidic monomers for use in preparing the polymeric gelling agents used in this invention include those listed in U.S. Pat. No. 4,654,039, entitled "Hydrogel-Forming Polymer Compositions For gel_ling agents used in this invention include those listed in U.S. Patent Use In Absorbent Structures", which issued to Brandt, Goldman and Inglin on Mar. 31, 1987. Preferred monomers include acrylic acid, methacrylic acid, and 2-acrylamido-2-methyl propane sulfonic acid. Acrylic acid itself is especially preferred for preparation of the polymeric gelling agent material.

Preferred polymer gelling agents which can be prepared from conventional types of monomers include hydrolyzed acrylonitrile grafted starch, polyacrylate grafted starch, polyacrylates, maleic anhydride-based copolymers and combinations thereof. Especially preferred are the polyacrylates and polyacrylate grafted starch. Examples of such preferred gelling agents are Aquakeep 10 SH, a cross-linked sodium polyacrylate supplied by Atochem S.A., 4 Cours Michelet, La Defense, Paris, France, and Sanwet IM5600-S, a cross-linked starch grafted sodium polyacrylate supplied by Farbwerke Hoechst AG of Frankfurt, Germany.

The preferred hydrogel-forming polymeric gelling agents used in the absorbent body 34 herein, will in general be slightly cross-linked. Cross-linking serves to render such hydrogel-forming polymer gelling agents substantially water-insoluble, and cross-linking thus in part determines the gel volume and extractable polymer characteristics of the hydrogels formed from the polymeric gelling agents employed. Suitable cross-linking agents are well known in the art and include, for example, those described in greater detail in U.S. Pat. No. 4,076,663, which patent issued to Masuda et al. on Feb. 28, 1987.

Preferred cross-linking agents are the di- or polyesters of unsaturated mono- or polycarboxylic acids with polyols, the bisacrylamides and the di- or triallyl amines. Especially preferred cross-linking agents are N, N'-methylenebisacrylamide, trimethylol propane triacrylate and triallyl amine. The cross-linking agent generally comprises from 0.001 mole percent to 5.0 mole percent of the resulting hydrogel-forming polymer material. More preferably, the cross-linking agent will comprise from 0.01 mole percent to 3.0 mole percent of the hydrogel-forming polymeric gelling agent used herein.

The slightly cross-linked, hydrogel-forming polymeric gelling agents which are the preferred absorbent materials for use in the articles of the present invention are generally employed in their partially neutralized form. For the purposes of this invention, such materials are considered partially neutralized when at least 25.0 mole percent, and preferably at least 50.0 mole percent of monomers used to form the polymer are acid group-containing monomers which have been neutralized with a salt-forming cation. Suitable salt-forming cations include alkali metal, ammonium, substituted ammonium, and amines. This percentage of the total monomer utilized which are neutralized acid group-containing monomers is referred to herein as the "degree of neutralization".

Irrespective of their composition and nature, particulate polymeric gelling agents for use in catamenial devices in accordance with the present invention must possess a gel strength above a defined minimum and must maintain gel strength above this minimum after absorption of aqueous liquid discharged by the wearer.

For the purposes of the present invention, the water insoluble particulate hydrogel material must have a gel strength of at least 0.38 kPa after 5 minutes exposure to a synthetic urine solution in the modified Absorbent Gel Expansion Pressure Test (AGEP test) defined hereinafter. Further, the water insoluble hydrogel material must have a gel strength of at least 0.38 kPa after 30 minutes exposure to a synthetic urine solution in the AGEP test. Preferably the gel strength of the hydrogel after 5 minutes exposure should be at least 0.48 kPa and more preferably is at least 0.54 kPa. Mixtures of different polymeric gelling materials having different compositions may be used provided that each satisfies the above requirements.

A characteristic of hydrogel materials useful for the purposes of the present invention is that the gel strength of the fully saturated material (e.g. after 30 minutes exposure) should not be less than the minimum value of 0.38 kPa required for unsaturated material (i.e. after 5 minutes exposure). However preferred hydrogel materials show a generally regular increase in gel strength from the value after 5 minutes exposure to the value after 30 minutes exposure. Preferably this increase is at least 25%, more preferably is at least 50% and most preferably is at least 75% of the value after 5 minutes exposure.

The modified AGEP test measures the force exerted by the gel as it expands following exposure absorption to a synthetic urine solution. The force is measured by a circular pressure foot that fits closely within a 2 cm diameter sample cell of an Ametek Precision Stage Model C1395X available from Ametek Corporation, Mansfield & Brown Division, 8600 Somerset Drive, Largo, Fla. 36543, USA. The Force gauge is an 'Accuforce' device available from Brown Tool & Supply Co, Solon, Ohio, USA.

The following procedure is used:

1. Weigh out 0.179 g±0.001 g polymeric gelling agent material into the absorption cell.

2. Place the cell containing the sample in the sample alignment bracket on the precision stage of the Ametek, and line up the sample holder so that the pressure foot will be centred when in the tube.

3. Add a 56 x load (10 ml) of Jayco synurine (see note 1) to the sample.

4. Using the lever on the Ametek stand, raise the sample until the foot is almost touching the fluid.

5. Zero and clear the Ametek Force Gauge and if using a chart recorder start it with the speed set to 1 cm/min.

6. Turn the illuminator on.

7. Using the coarse and fine adjustments on the precision stage, raise the sample until the level of the fluid is even with the top of the foot. This is achieved by sighting across the foot. The fluid that is on the wall of the absorption all due to the surface tension will appear as a white band. As this band moves up the cell it will block the silver colour of the foot. When the white band is above the top of the foot a silver band will reappear. At this point lower the sample using the fine adjuster until the silver band disappears.

8. Turn off the illuminator immediately.

9. When the gel reaches the foot, set the timer for 30 minutes and start It.

10. At the end of 5, 10, 15, 20 and 30 minutes record the force in grams.

Calculations

Pressure=Reading of Machine (g) /area of foot ($cm^2$)× 98.1 (kPa)

Notes

1. Jayco Synurine

The Jayco Synurine is made up with the following quantities of compounds per liter of solution.

| | |
|---|---|
| $Na_2SO_4$ | 2.0 g/l |
| KCl | 2.0 g/l |
| $(NH_4)_2HPO_4$ | 0.15 gli |
| $(NH_4)H_2PO_4$ | 0.85 g/l |
| $MgCl_2{:}6H_2O$ | 0.5 g/l |
| $CaCl_2{:}2H_2O$ | 0.25 g/l |

2. Testing should be conducted with the equipment and sample at a stable temperature of 25° C.

3. The tube internal diameter is 2 cm so that the surface area of the foot is 3.14 $cm^2$.

The polymeric gelling agent materials used in the absorbent articles herein must be able to imbibe fluids encountered in such articles and more particularly must give the absorbent body a sufficiently high capacity for such fluids to permit absorption of medium to high menstrual flows.

Absorption is a physical phenomenon and is determined by the physical characteristics of the liquid and the absorbent substrate. Although menses is an aqueous-based body fluid its complex composition comprising mineral salts, suspended proteinaceous solids and partially solubilised liquid components makes standardisation of absorption determination difficult. This difficulty is compounded by differences between individuals so that reproducible quantitative results are, in practice, virtually impossible to obtain. Accordingly, screening tests have to be adopted in which model fluids are used to provide absorption data that are correlatable with user experience.

One such screening test that has been found to be useful measures the Retention Capacity of polymeric gelling agent material under a centrifugal load. This has been found to be more predictive of the absorption capacity of the material in a sanitary napkin than the equilibrium absorbent capacity which represents the maximum weight of fluid that the polymeric gelling material is capable of retaining in the absence of any imposed load.

In the Retention Capacity test, a 0.2 g sample of polymeric gelling agent is placed in a heat sealable non woven pouch comprising a tea bag available as Dexter 1234 - Heat Sealable from Dexter Corporation, Windsor Locks, Conn. 06096, USA.. The tea bag is sealed and immersed in a 0.9% saline solution at 20° C. for 20 minutes. The tea bag is then centrifuged for 3 minutes at 1400 RPM in a centrifuge drum of diameter 23 cm, providing a force of 250x gravity. A blank sample, i.e. an identical tea bag containing no polymeric gelling agent, is given the same treatment and the difference in weight between the two samples, less the weight of the dry polymeric gelling agent, represents the fluid retained by the gelling agent. From this value the Retention Capacity can be calculated in g fluid/g dry polymeric gelling agent. For the purposes of this test dry polymeric gelling agent is taken to be the material as supplied although this may incorporate up to 5% by weight of moisture.

Polymeric gelling agent materials useful in the present invention should preferably have a Retention Capacity as measured in the above described test of at least 10 g/g, more preferably at least 20 g/g and most preferably at least 30 g/g.

Whilst the above defined Retention Capacity values represent preferred minimum requirements for polymeric gelling agent materials to be useful in a sanitary, napkin in accordance with the present invention, the Retention Capacity test is not by itself predictive of the suitability of such materials. One reason for this is the different physical characteristics of the saline solution used as a model for urine, and menses fluid.

Accordingly, the Applicant has found it desirable to employ an additional absorbency screening test to assess the suitability of polymeric gelling materials for the purposes of the present invention.. This test comprises a measurement of the total storage capacity of a sanitary, napkin incorporating the polymeric gelling agent, using sheeps blood as the liquid to be absorbed.

Sheeps blood is a labile material having a limited life even when stored under appropriate conditions. It comprises a heterogeneous mixture of approximate composition 15% by weight haemoglobin and 75–80% by weight water with low levels of ionic salts, lactic acid and urea.

For the purposes of absorbency, testing for the present invention, fresh whole sheeps blood is employed. The blood may be stored at 4° C.±1° C. in a sealed container and is discarded after two weeks if not used. Testing is carried out at a liquid temperature of 22° C.±1° C., and for this purpose a sealed container is removed from storage in advance of the testing, warmed in a water bath and shaken to ensure uniform distribution of the components of the blood prior to the contents being poured into the vessel in which the testing takes place.

In the test, 1 liter of the sheeps blood is poured into a fiat vessel of surface area greater than the area in plan of a sanitary napkin, and a napkin is weighed and then placed with the fluid permeable topsheet facing downwards on the surface of sheeps blood in the vessel. The napkin is left for 20 minutes after which the saturated napkin is removed and placed with its fluid-permeable topsheet surface uppermost, on a slightly inclined rigid planar surface. The topsheet surface of the napkin is then subjected to a load of 17 g/cm$^2$ applied via a plate of the same surface area as the napkin. The plate is a composite structure comprising a rigid material with a layer of resilient foam on its lower surface and a fluid impermeable plastics film on the lower surface of the foam to prevent absorption of the blood by the foam. The load is maintained for two minutes and the napkin is then removed and weighed to obtain the quantity of sheeps blood absorbed and retained under load. The difference between the dry and loaded weights of the napkin is taken to be the Total Storage Capacity of the napkin.

For the purposes of the test a model sanitary napkin is prepared comprising a non-absorbent fluid-permeable topsheet, a hydrophilic fluid-permeable acquisition sheet underlying the topsheet, an absorbent core assembly composed of particulate gelling agent sandwiched between two layers of cellulosic tissue and a fluid impermeable backsheet underlying the core assembly.

The topsheet and backsheet extend outwardly of the edges of the core assembly and the acquisition sheet and are secured together around their periphery to envelop the core assembly and acquisition sheet.

The air laid tissue component of the absorbent core assembly comprises an air laid wet-strength cellulosic web of basis weight 63 g/m$^2$ having a length of 207 mm and a width of 150 mm. A hot melt adhesive (Fuller HL 1222) is applied to one surface of the web to give a longitudinally extending band of width approximately 130 mm at an application rate of 4 g/m$^2$ (0.14 g).

Particulate polymeric gelling material is deposited on the adhesively coated web surface at a loading of approximately 58.5 g/m$^2$ in the form of a longitudinally extending band of width 70 min. The side edge portions of the web that are free of gelling material are then folded inwardly to cover the upper surface of the band of polymeric gelling material, thus forming an upper tissue layer. The side edges of the web overlap to a small extent in the area of the longitudinal centre line of the absorbent core assembly. The folded tissue - polymeric gelling material laminate is provided with rounded ends by the web with a curved edge cutter of radius approximately 38 mm. This leaves a tissue laminate having a loaded surface area in plan of 136.5 cm$^2$ containing 0.8 g of polymeric gelling material.

A 70/30 rayon/polyester non woven spun laced fabric of basis weight 51 g/m$^2$ is used to form the fluid-permeable acquisition sheet. This sheet has a 'dog bone' shape of overall length 207 mm, a minimum width at the centre of 76 mm and rounded ends of maximum width 86 min. The sheet weight is 0.79 g and the total weight of the acquisition sheet, tissue layers and gelling agent is 3.44 g.

For the purposes of the present invention the Total Storage Capacity for a napkin incorporating 0.8 g of polymeric gelling agent should be at least 40 g, preferably at least 45 g and most preferably at least 50 g of sheeps blood in the above test.

Another important in-use characteristic of a polymeric gelling agent material is the rate at which it is capable of absorbing liquid when incorporated in a napkin up to the point at which the napkin becomes completely saturated (i.e. its Total Storage Capacity). This is a function of the susceptibility of the gelling agent material to gel blocking and hence, indirectly, a function of the gel strength of the gelling agent material. However different polymeric gelling materials display different gel strength behaviour patterns on absorption of liquid, even when the initial (5 minute) gel strength values of the materials are similar. In consequence, the time taken by different polymeric gelling agents to absorb a given volume of liquid, hereinafter referred to as the Acquisition Time, will vary. The Acquisition Time is also likely to be different for any particular polymeric gelling material at different levels of uptake of liquid. Nevertheless, sanitary napkins incorporating high gel strength materials are likely to display higher rates of absorption, i.e. lower Acquisition Times, than materials of lower gel strength, because of the diminished effect of gel blocking.

The test to measure the Acquisition Time is carried out by applying successive 5 ml aliquots of sheep blood fluid to the topsheet surface of a sanitary napkin containing a polymeric gelling agent as the absorbent species, and recording the time taken for each successive aliquot to be absorbed by the gelling agent. This measurement is repeated for a similar sanitary napkin containing no polymeric gelling agent to provide a base-line value. A model sanitary napkin having a structure and composition as described above in connection with the Total Storage Capacity Test is used to measure Acquisition Times.

Sanitary napkins containing the preferred polymeric gelling agents have Acquisition Times whose values are lower than those for sanitary napkins containing non-preferred polymeric gelling agents. For polymeric acid based materials the Acquisition Time values are close to the base line value for the aliquot concerned.

For the purposes of the test, a model sanitary napkin is prepared, comprising a non absorbent, fluid permeable topsheet, a fluid permeable acquisition sheet, underlying the topsheet, a fluid impermeable backsheet and an absorbent core disposed between the backsheet and the fluid acquisition sheet.

The absorbent core comprises two layers of wet strength cellulosic tissue of basis weight 63 g/m$^2$ between which a layer of particulate hydrogel material is disposed at a loading of 58.5 g/m$^2$ to give a total hydrogel weight of 0.8 g and a total absorbent body weight of 3.44 g.

The apparatus consists of a flat horizontal plate upon which a napkin is placed in a flat configuration with the fluid permeable topsheet uppermost. A second flat plate overlies the first and is capable of being loaded so as to provide a pressure of 17 g/cm$^2$ based on the plan area Of the napkin. The upper plate is formed with a recess at the intersection of its longitudinal and lateral axes, the recess being capable of holding at least 5 ml of liquid, and the recess is provided with a centrally located orifice in its base.

To carry out the test, a napkin is placed between the two plates, so that its central region underlies the orifice, the upper plate is loaded to provide a pressure of 17 g/cm$^2$ on the napkin and 5 ml of sheep blood at a temperature of 22° C.±1° C. is added to the central recess in the upper plate from a hand held container.

A stop watch is started as the sheep blood is added, and stopped when visual observation of the surface of the topsheet in the region of the orifice shows that all of the added liquid has passed through the topsheet. Successive 5 ml aliquots of liquid are added and the times for their absorption are measured in the same way until a total of 20 ml of sheep blood has been absorbed by the napkin.

The results are used to compare the rate of liquid uptake by various polymeric gelling materials. In principle, preferred polymeric gelling materials have higher overall rates of uptake, i.e. take less time to absorb 20 ml of sheep blood. However, for two materials having the same overall rate of uptake, the material having the higher initial rate, i.e. for the uptake of the first 10 ml is preferred. Acquisition times of less than about 30 seconds are preferred for uptake of the 5 ml aliquot providing a total liquid uptake of 10 ml.

The mean particle size and particle size distribution of hydrogel materials useful in the present invention can, with; advantage differ from conventional practice. The mean particle size preferably lies within the range from 100 micrometers to 250 micrometers, with less than 1% by weight being greater than 800 micrometers in size, 99% by weight lying within the range 800 micrometers to 50 micrometers and less than 1% by weight being less than 50 micrometers in size.

Within the webs which form the layers of the absorbent body 34, the particles of the polymeric gelling agent should be thoroughly dispersed but may or may not be uniformly distributed. In particular, there may be regions or zones of the core layers which have higher concentrations of gelling agent particles than do other regions or zones of the layers. However, it should be noted that the scope of the present invention is not intended to extend to sanitary, napkins which are void of any superabsorbent material and which have a central absorbent member overlaid solely by nonwoven materials, wherein the nonwoven materials have caliper of less than 0.50 millimeters, as determined by the caliper test, as later defined.

Superimposed over the absorbent body 34 is a liquid permeable wipe acquisition sheet 28. In a preferred embodiment, the wipe acquisition sheet 28 is a nonwoven sheet. In the preferred embodiment shown in FIG. 2, the sheet 28 is a spunlaced 70%/30% rayon/polyester fiber sheet. Spunlaced fabrics of this type are manufactured by E.I. DuPont Nemours & Company of Wilmington, Del., and are made available under the tradename"SONTARA" (SONTARA registered ™ by E.I. DuPont Nemours & Company). These fabrics are available in a number of suitable styles, but, Style 8407 in its apertured form, having a basis weight of 0.005 grams per square centimeter and a thickness of 0.55 millimeters, is preferred. The wipe acquisition sheet 28 extends beyond the edges of the wet-laid tissue 31 where it too is associated with the barrier sheet 16. The wipe acquisition sheet 28 greatly improves lateral wicking of exudates over the absorbent body 34 thereby providing a more even distribution of the exudates throughout the absorbent body 34. The lateral wicking of the wipe acquisition sheet 28 is important for the following reason. Many bulky prior art sanitary napkins rely on a high degree of vertical absorption at the point where exudates are initially deposited. In other words, because the absorbent cores of these napkins are fairly thick, they can absorb a high degree of exudates throughout their thickness while utilizing only a small degree of their surface area or lateral absorption capability. However, the relatively thin napkin 10 of the present invention have a comparatively small degree of vertical absorption. Therefore, for a relatively large amount of exudates to be absorbed, a wipe acquisition sheet 28 which can laterally disperse the exudates over a large surface area of the absorbent body 34 where the exudates can better and faster be vertically absorbed is highly desirable. Further, the wipe acquisition sheet 28 provides a fairly high degree of initial absorption during the time interval between the time exudates are deposited onto the topsheet 25 and the time they are absorbed by the absorbent body 34. This property will be more specifically described later. Superimposed over the wipe acquisition sheet 28 is the liquid permeable topsheet 25. In a preferred embodiment, the topsheet 25 is associated with the wipe acquisition sheet 28 by spray-gluing the topsheet 25 to the surface of the wipe acquisition sheet 28. The topsheet 25 is compliant, soft feeling, and non-irritating to the wearer's skin. Further, the topsheet 25 is liquid pervious, permitting liquid to readily transfer through its thickness. A suitable topsheet 25 may be manufactured from a wide range of materials such as polymeric materials, formed thermoplastic films, porous foams, reticulated foams, natural fibers (e.g. wood or cotton fibers), synthetic fibers (e.g. polyester or polypropylene fibers) or from a combination of natural and synthetic fibers, with apertured formed films being preferred. Formed films are preferred for the topsheet 25 because they are pervious to liquids and yet non-absorbent. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structure Having Tapered Capillaries", which patent issued to Thompson on Dec. 30, 1975, U.S. Pat. No. 4,324,246, entitles "Disposable Absorbent Article Having A Stain Resistant Topsheet", which patent issued to Mullane and Smith on Apr. 13, 1982, U.S. Pat. No. 4,342,314, entitled "Resilient Plastic Web Exhibiting Fiber-Like Properties", which patent issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which patent issues to Ahr, Louis, Mullane, and Ouellete on Jul. 31, 1984.

In a preferred embodiment of the present invention, the body surface 26 of the topsheet 25 is hydrophilic. The hydrophilic body surface 26 helps liquid to transfer through the topsheet 25 faster than if the body surface 26 was not hydrophilic. This diminishes the likelihood that menstrual fluid will flow off the topsheet 25 rather than being absorbed by the absorbent body 34. In a preferred embodiment, the body surface 26 of the topsheet 25 is made hydrophilic by treating the body surface 26 with a surfactant. It is preferred that the surfactant be substantially evenly and completely distributed throughout the body surface 26 of the topsheet 25. This can be accomplished by any of the common techniques well known to those skilled in the art. For example, the surfactant can be applied to the topsheet 25 by spraying, by padding, or by the use of transfer rolls. Further, the surfactant can be incorporated into the polymeric materials of a formed film topsheet or between or within the fibers of a nonwoven topsheet.

The barrier means 16 is disposed adjacent the second major surface 22 of the absorbent means 13. In a preferred embodiment, the absorbent means 13 may be affixed over the second major surface 22 of the absorbent means 13 to the barrier means 16. Any of the common techniques well known in the art, such as spray-gluing or lines or spots of adhesive may be used for this purpose. The barrier means 16 generally defines the garment surface 17 of the sanitary napkin 10. The barrier means 16 may be any means which is impervious to liquids and which prevents exudates absorbed and contained in the absorbent means 13 from soiling articles, such as panties, which come in contact with the garment surface 17 of the sanitary napkin 10. In the preferred embodiment of the sanitary napkin 10 illustrated in FIGS. 1 and 2, the barrier means 16 is a barrier sheet manufactured from a thin plastic film. Other flexible liquid impervious materials may also be used. Preferably, the barrier sheet 16 is a polyethylene film having a thickness of from 0.012 millimeter to about 0.051 millimeter. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The barrier sheet 16 is preferably embossed and/or matte finished to provide a more clothlike appearance. Further, the barrier sheet 16 may permit vapors to escape from the absorbent means 13 while still preventing exudates from passing through the barrier sheet 16.

Preferably, the topsheet 25 and the barrier sheet 16 have length and width dimensions generally larger than the absorbent body 34 so that they extend beyond the edges 52 and 55 of the absorbent body 34 where they are associated together in a suitable manner. As used herein, the term "associated" encompasses configurations whereby a first member is directly joined to a second member and configurations whereby a first member is indirectly joined to a second member by affixing the first member to intermediate members which in turn are affixed to the second member. The extension of the topsheet 25 and/or the barrier sheet 16 beyond the end edges 52 and the side edges 55 of the absorbent body 34 form the end edges 11 and the side edges 12, respectively, of the sanitary napkin 10. In a preferred embodiment, the barrier sheet 16 and the topsheet 25 have an elliptical shape and extend beyond the absorbent body 34 by a distance of at least 1.0 centimeter to form a peripheral margin where they are joined directly to each other by attachment means as are well known in the art. The attachment means may employ an adhesive in the form of a uniform continuous layer, a patterned layer or an array of separate lines or spots or may utilise heat and/or pressure to fuse the two sheets together, or may crimp the sheets together mechanically.

The sanitary napkin 10 of the present invention preferably has a low flexure-resistance. Thus, the sanitary napkin 10 of the present invention is highly flexible and conforms very well to the various shapes of the female urogenital region. Preferably, the sanitary napkin 10 of the present invention has a flexure-resistance of less than 300.0 grams, more preferably less than 250.0 grams, and still more preferably less than about 175.0 grams and most preferably less than 130.0 grams.

The flexure-resistance of a sanitary napkin is measured by peak bending stiffness. Peak bending stiffness is determined by a test which is modelled after the ASTM D 4032-82 CIRCULAR BEND PROCEDURE, the procedure being considerably modified and performed as follows. The CIRCULAR BEND PROCEDURE is a simultaneous multidirectional deformation of a material in which one face of a specimen becomes concave and the other face becomes convex. The CIRCULAR BEND PROCEDURE gives a force value related to flexure-resistance, simultaneously averaging stiffness in all directions.

APPARATUS

The apparatus necessary for the CIRCULAR BEND PROCEDURE is a modified Circular Bend Stiffness Tester, having the following parts:

A smooth-polished steel plate platform which is 102.0 x 102.0 x 6.35 millimeters having an 18.75 millimeter diameter orifice. The lap edge of the orifice should be at a 45 degree angle to a depth of 4.75 millimeters.

A plunger having an overall length of 72.2 millimeters, a diameter of 6.25 millimeters, a ball nose having a radius of 2.97 millimeters and a needle-point extending 0.88 millimeter therefrom having a 0.33 millimeter base diameter and a point having a radius of less than 0.5 millimeter, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), then the needle-point should not be used. The bottom of the plunger should be set well above the top of the orifice plate. From this position, the downward stroke of the ball nose is to the exact bottom of the plate orifice.

A force-measurement gauge and more specifically an Instron inverted compression load cell. The load cell has a load range of from 0.0 to 2000.0 grams.

An actuator, and more specifically the Instron Model No. 1122 having an inverted compression load cell. The Instron 1122 is made by the Instron Engineering Corporation, Canton, Mass.

NUMBER AND PREPARATION OF SPECIMENS

In order to perform the procedure for this test, as explained below, five representative sanitary napkins are necessary. From one of the five napkins to be tested, some number "Y" of 37.5×37.5 millimeter test specimens are cut. Specimens having portions in which a topsheet is joined directly to a barrier sheet or which are a laminate of a topsheet, two or less tissue sheets and a barrier sheet, should not be tested. The reason that these specimens are not tested is due to the realization that prior art napkins exist in which a topsheet is joined to a barrier sheet beyond the edges of an absorbent core in the periphery of the napkin, such portions of which are highly flexible. However, the present invention is more concerned with the overall flexibility of the sanitary napkin and not merely the peripheral portions thereof and, therefore, the flexibility of the present invention is more concerned with the flexibility of the significant absorbent portions of the sanitary napkin. If any of these significant absorbent portions of the sanitary napkin meet the parameters of this test, then the sanitary napkin satisfies the test. Therefore, a number of different specimens should be tested from each sanitary napkin. Certainly, the structurally most flexible portion of the sanitary napkin should be tested, excluding those-portions excluded above. The test specimens should not be folded or bent by the test person, and the handling of specimens must be kept to a minimum and to the edges to avoid affecting flexural-resistance properties. From the four remaining sanitary napkins, an equal number "Y" of 37.5×37.5 millimeter specimens, identical to the specimens cut from the first napkin, are cut. Thus, the test person should have "Y" number of sets of five identical specimens..

PROCEDURE

The procedure for the CIRCULAR BEND PROCEDURE is as follows. The specimens are conditioned by leaving them in a room which is 21°±1° C. and 50±2% relative humidity for a period of two hours. The test plate is levelled. The plunger speed is set at 50.0 centimeters per minute per full stroke length.

A specimen is centered on the orifice platform below the plunger such that the body surface 26 of the specimen is facing the plunger and the garment surface 17 of the specimen is facing the platform. The indicator zero is checked and adjusted, if necessary. The plunger is actuated.

Touching the specimen during the testing should be avoided. The maximum force reading to the nearest gram is recorded. The above steps are repeated until all five of the identical specimens have been tested.

CALCULATIONS

The peak bending stiffness for each specimen is the maximum force reading for that specimen. Remember that "Y" number of sets of five identical specimens were cut. Each set of five identical specimens is tested and the five values received for that set are averaged. Thus, the test person now has an average value for each of the "Y" sets tested. Remember, if any of the significantly absorbent portions of the sanitary napkin have the requisite flexure-resistance, then the napkin satisfies the parameters of this test. Therefore, the flexure-resistance for a particularly designed sanitary napkin is the greatest of these average peak bending stiffnesses.

Figure 3:
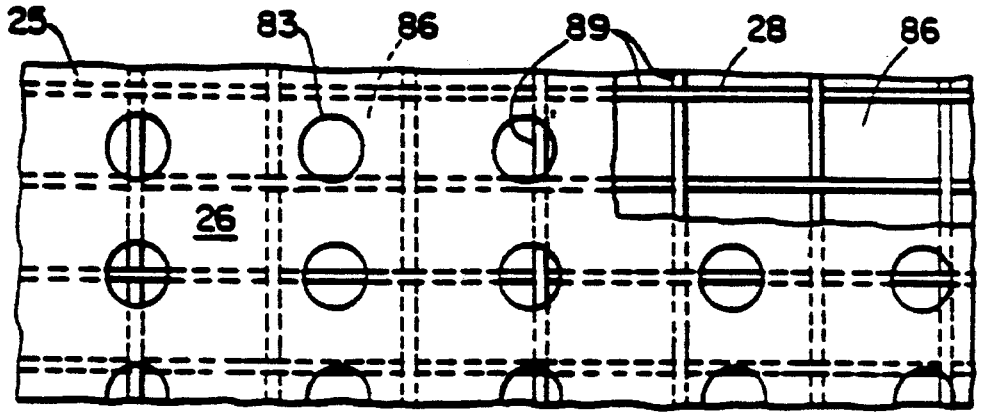
FIG. 3 is a top plan view of a preferred topsheet and wipe acquisition sheet laminate with portions of the topsheet being torn away to show underlying structure.

As alluded to earlier, the combination of topsheet 25 and wipe acquisition sheet 28 imparts some beneficial properties to the sanitary napkin 10. In particular, the combination of an apertured formed film topsheet 25 superimposed over an apertured nonwoven wipe acquisition sheet 28 is beneficial. A preferred wipe acquisition sheet 28 is the previously described SONTARA 8407. An enlarged depiction of such an arrangement is shown in FIG. 3. Such a combination is even more beneficial when the nonwoven wipe acquisition sheet 28 is formed or positions such that no fiber bundles 89 of the sheet 28 are beneath some of the apertures 83 of the formed film topsheet 25 (i.e. the apertures in the two sheets 25 and 28 are aligned) while beneath other apertures 83 of the formed film topsheet 25 fiber bundles 89 of the nonwoven sheet 28 are present (i.e. apertures in the two sheets 25 and 28 are not aligned). Such an arrangement is readily apparent in FIG. 3, wherein the apertures 86 of the nonwoven sheet 28 are larger than the apertures 83 of the formed film topsheet 25. Such an arrangement provides the sanitary, napkin 10 at least two beneficial properties: enhanced gush acquisition and enhanced wipe acquisition. Gush acquisition is enhanced in those areas where the apertures 83 of the topsheet 25 are aligned with the apertures 86 of the nonwoven wipe acquisition sheet 28. The aligned apertures 83 and 86 provide a direct route for exudates to flow from the body surface 26 of the topsheet 25 to the central absorbent materials of the napkin 10. Further, the apertures 83 and 86 themselves are able to contain a degree of fluid within their walls or boundaries until such fluid is absorbed. Wipe acquisition, which is the ability to pull liquid exudates from the wearer's skin into the absorbent material of the napkin 10, is enhanced in those areas where fiber bundles 89 of the nonwoven wipe acquisition sheet 28 are aligned such that the fiber bundles 89 are beneath the openings of the apertures 83 of the topsheet 25.

As just mentioned, wipe acquisition is critical in those regions where the topsheet 25 is in contact with exudates on the wearer's skin. In such areas, the sanitary napkin 10 is likely under compressive forces from the wearer's body. When such is the case, the fiber bundles 89 of the nonwoven wipe acquisition sheet 28 beneath the apertures 83 of the topsheet 25 are forced somewhat up into the apertures 83 of the topsheet 25, closer to the wearer's skin. Obviously, the spaces between the fiber bundles 89 and the walls of the apertures 83 or between the fibers of the fiber bundles 89 themselves will be less than the spaces which were between only the walls of the apertures 83. These spaces are capillaries. As is well known in the art, as capillary spaces are decreased, capillary or drawing action is increase. Thus, the capillary action in these apertures 83 where fiber bundles 89 are present is increased and the sanitary napkin 10 is better able to draw exudates from the wearer's skin into these capillaries and eventually into the central absorbent materials of the sanitary napkin 10.

Although all of the apertures 83 of the topsheet 25 are referenced by the numeral "83", for the following teaching purposes, specific reference is directed to the aperture of FIG. 3 specifically labelled and designed "83". The specific aperture 83 referenced is an example in which an aperture 83 of the topsheet 25 is aligned with an aperture 86 of the nonwoven wipe acquisition sheet 28. Theoretically, such an aperture is useful for gush acquisition since exudates have uninterrupted flow form the body surface 26 of the topsheet 25 to the central absorbent material (not shown). Next, attention is directed to the aperture 83 immediately to the right of the specific aperture 83 just referenced. As seen, this aperture 83 will enter the capillaries of the fiber bundle 89. The exudates will then either be pulled or absorbed into the central absorbent materials or wicked to intersecting fiber bundles 89, then wicked further to other intersecting fiber bundles 89, and so on, until the exudates are absorbed into a more laterally distant portion of the central absorbent materials. Hence, a large portion of the total absorbent capacity of the absorbent materials can be utilized.

As previously mentioned, the sanitary napkin 10 of the present invention has a liquid capacity great enough to absorb medium to high menstrual flows. As noted hereinbefore, measurement of the Total Storage Capacity of the sanitary napkin 10 is carried out using sheep blood as the liquid absorbate. Sanitary napkins in accordance with the invention should have a Total Storage Capacity of at least 40 g more preferably at least 45 g and most preferably at least 50 g.

The central absorbent width 63 of the sanitary napkin 10 of the present invention is believed to be an important parameter for the following reason. The sanitary napkin 10 of the present invention relies more on the lateral distribution of exudates over or through a relatively large surface area of the absorbent core 34 rather than on a high degree of vertical absorption common to many prior art sanitary napkins. Therefore, because exudates which are distributed onto the topsheet 25 may not be quickly absorbed before they migrate across the topsheet 25, it is important to contain such exudates pending absorption. The specified central absorbent width 63 of the sanitary napkin 10 of the present invention has been determined based on the width of a flexible napkin which will cup around the labia in the region of the vaginal orifice such that at least the edges of the absorbent material are positioned in the uppermost part of the wearer;s legs at the crotch. Thus, the sanitary, napkin 10 and the absorbent material may be cupped shaped in the surrounding regions of the vaginal orifice and exudates deposited thereon will be contained until absorbed.

Determination of the central absorbent width of the sanitary napkin is carried out as follows, reference being made to FIG. 5. A point 64 on the sanitary napkin 10 which is disposed beneath the center of the vaginal orifice, when worn, is located. A plane 65 parallel to the lateral centerline 61 and 3.75 centimeters forward from the point 64 in the direction of the wearer's mons pubis is located. Another plane 66 parallel to the lateral centerline 61 and 5.0 centimeters rearward from the point 64 in the direction of the wearer's buttocks is also located. The greatest fiat-out, uncompressed, unmanipulated, lateral dimension of absorbent material of the sanitary napkin 10 between the planes 65 and 66 is the central absorbent width 63 of the sanitary napkin 10. The absorbent material may be a single sheet, etc., and the absorbent material may be in the form of a nonwoven sheet, an absorbent topsheet, and absorbent core, a tissue, synthetic staple fibers, etc. For example, a sanitary napkin 10 of the present invention might have a wipe acquisition sheet 28 having a width of 7.75 centimeters and an absorbent body 34 having a width of 7.0 centimeters. Thus, in this example, the sanitary napkin 10 has a central absorbent width 63 of 7.75 centimeters.

The sanitary napkin 10 should preferably be scaled to the width of the crotch of the underwear of the wearer. A sanitary napkin 10 having a central absorbent width 63 which registers the absorbent 13 with the edges of the underwear crotch is particularly preferred. For underwear crotches having a width of 4.0 to 8.0 centimeters, a sanitary napkin having a central absorbent width 63 of 4.0 to 8.0 centimeters works well.

The total width of the napkin 10 is scaled to the central absorbent width 63, and should be from 1.2 to 2.0 centimeters greater than the central absorbent width 63, due to the additional margin necessary to join the edges of the topsheet 25 and barrier sheet 16 together.

Generally 0.3 to 0.5 centimeters are necessary at each edge of the napkin 10 to join the topsheet 25 to the barrier sheet 16. Thus, a napkin having a central absorbent width 63 of 4.0 to 8.0 centimeters will have a total width ranging from 5.2 to 6.0 centimeters to from 8.2 to 10.0 centimeters.

The sanitary napkin 10 of one embodiment of the present invention intended for underwear having a relatively greater crotch width should have a central absorbent width 63 of at least 6.5 centimeters, more preferably of at least 7.0 centimeters, more preferably of at least 7.75 centimeters, and most preferably of at least 9.0 centimeters.

Preferred sanitary napkins in accordance with the present invention have low flexure resistance and, in consequence are likely to be relatively thin. Thin sanitary napkins are advantageous as they are unobtrusive and the user will have a low awareness of such sanitary napkins during the period of wear. The sanitary napkin 10 shown in FIGS. 1 and 2 has a caliper of approx. 2.7 millimeters. The caliper of a sanitary, napkin 10 is determined by the following test.

A comparator gauge, and specifically the Ames, Model 130 with dial indicator Model 482, available from the B.C. Ames, Company of Waltham, Mass. is needed. The comparator gauge should have a circular comparator foot made of aluminium and having a weight of 10.0 grams and a contact surface of 5.16 square centimeters. The comparator gauge is zeroed. An 80.0 grams stainless steel weight is place don the spindle extending above the comparator dial. The comparator foot is raised and the napkin, with any panty adhesive release paper being removed, is placed garment surface down on the base plate. The napkin is positioned on the base plate sot hat when the foot is lowered it is in the center of the napkin. Try to smooth out or avoid any wrinkles in the napkin. Gently lower the foot onto the napkin. Determine the napkin caliper by reading the comparator dial 30 seconds after the foot comes in contact with the napkin. Repeat the measurement 3.0 centimeters from each of the ends of the absorbent material along the longitudinal centerline 58 of the napkin. The average of the three readings is the caliper of the sanitary napkin.

Preferably, the sanitary napkin 10 of the present invention has a caliper of less than 3.0 millimeters, more preferably less than 2.5 millimeters. Increases in the caliper of the sanitary, napkin are generally less preferred and are proportional to increases in the flexure-resistence. Thus an increase in caliper to 4.5 or even 5.0 millimeters, would be accompanied by an increase in flexure resistance to 400 grams. However an increase in caliper above 3.5 mm is not preferred.

Figure 4:
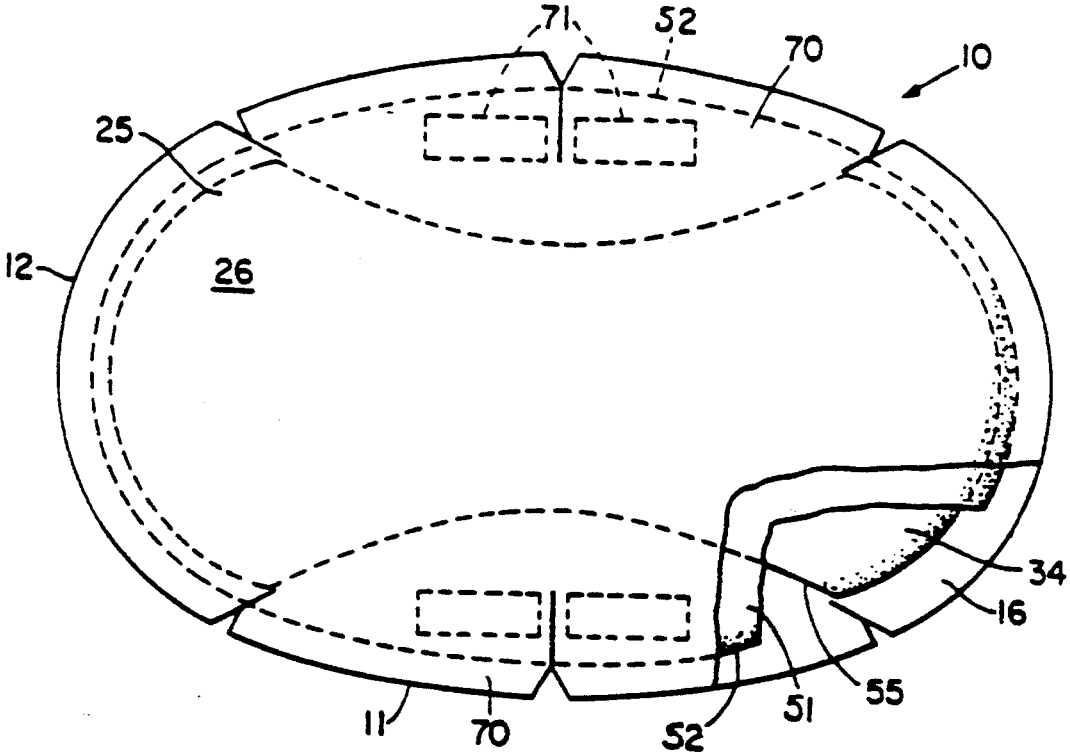
FIG. 4 is a top plan view of an alternatively preferred sanitary napkin embodiment of the present invention with portions being torn away to shown underlying structure.

An alternative embodiment of a sanitary napkin 10 of the present invention is shown in FIG. 4. In this embodiment, a tissue layer 51 is inserted between the absorbent body 34 and the topsheet 25 and the sanitary napkin 10 has two flaps 70 each of which are adjacent to and extend laterally from a side edge 55 of the absorbent body 34. The flaps 70 are configured to drape over the edges of the wearer's panties in the crotch region so that the flaps 70 are disposed between the edges of the wearer's panties and the wearer's thighs. The flaps 70 serve at least two purposes. First, the flaps 70 help serve to prevent soiling of the wearer's body and panties by menstrual fluid. Second, the flaps 70 are preferably provided with attachment means 71 on their garment surface 17 so that the flaps 70 can be folded back under the panty and attached to the garment facing side of the panty. In this way, the flaps 70 serve to keep the napkin 10 properly positioned in the panty. A preferred attachment means 71 is a pressure-sensitive adhesive, as is well known in the art. Alternatively, the flaps 70 may be attached to each other on the underside of the panty by the attachment means 71 being affixed to the panty.

In the embodiment shown, the flaps 70 are comprised of topsheet 25, tissue 51, and barrier sheet 16. Further, in the embodiment shown, the flaps 70 are unitary with the laminae of the napkin 10. In other word, the topsheet 25, tissue 51 and barrier sheet 16 simply extend laterally beyond the absorbent body 34 to form the flaps 70. However, the flaps 70 need not be unitary with the napkin 10 but can be separate elements which are affixed to the napkin 10. Further, the flaps 70 can be comprised of a single substrate or other laminae configurations. However, it is preferred that the flaps 70 have a liquid impervious barrier sheet 16. The barrier sheet 16 prevents exudates which reach the flaps 70 from soiling the edges of the wearer's panties. Further, it is preferable that the flaps 70 be provided with an absorbent layer, at least to a point beyond the edges of the wearer's panties. Theoretically, only a relatively small amount of menses should reach the flaps 70, therefore, only a relatively small amount of absorbent material is desirable in the flaps 70. However, for sanitary napkins intended for medium or heavy menstrual flows, it is preferred that the flaps 70 incorporate some absorbent material in order to prevent any exudates that reach the flaps from being able to flow further to unprotected areas. The absorbent material may be a tissue, or an extension of the absorbent body 34, such as the tissue-forming the layers 40 & 43. However, the absorbent material in the flaps 70 should not significantly impair the flexibility of the flaps.

A number of sanitary napkins having flap designs suitable or adaptable for use with the sanitary napkins 10 of the present invention are known. Examples of sanitary napkins with such flap designs are disclosed in U.S. Pat. Nos. 4,687,478, 4,608,047 and 4,285,343.

For illustration purposes, the central absorbent width 63 of the napkin 10 shown in FIG. 4 would extend laterally from the outer edge 52 of the tissue 51 in the one flap 70 to the outer edge 52 of the tissue 51 in the other flap 70.

Figure 5:
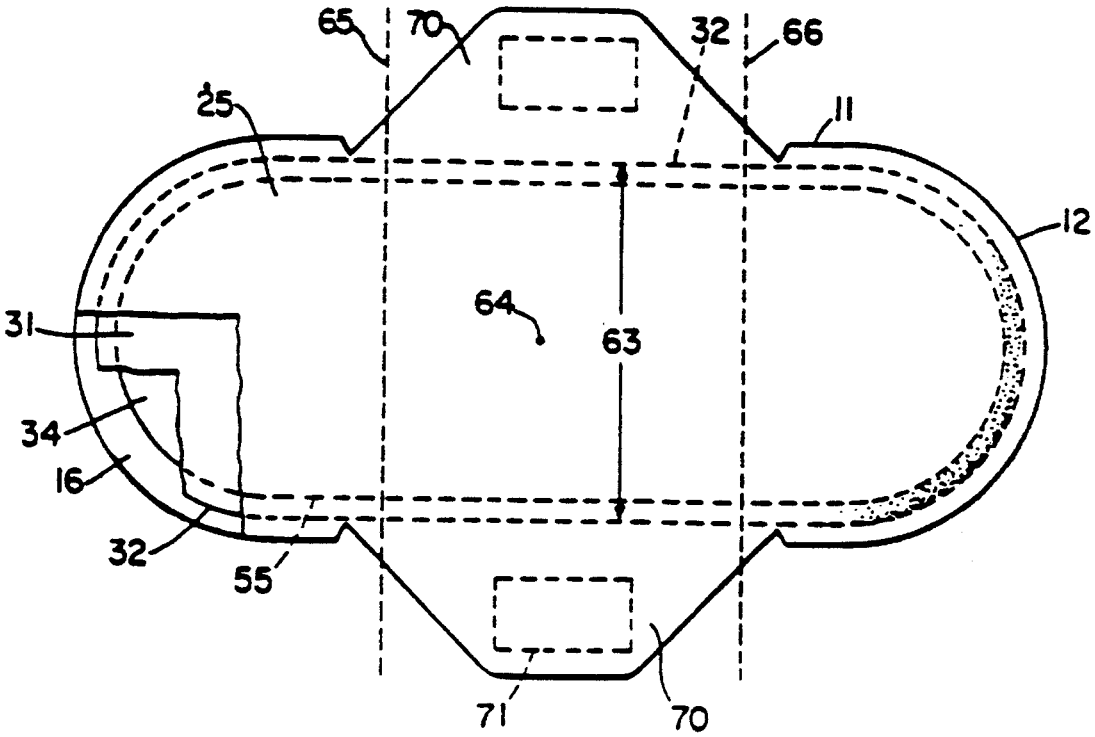
FIG. 5 is a top plan view of another alternatively preferred sanitary napkin embodiment of the present invention with portions being torn away to show underlying structure.

Another alternative embodiment of a sanitary napkin 10 of the present invention is shown in FIG. 5. Like the napkin 10 shown in FIG. 4, this napkin 10 also has flaps 70, only of a different configuration. In this embodiment, the flaps 70 are comprised only of the topsheet 25 and the barrier sheet 55.

For illustrative purposes, the central absorbent width 63 of the napkin 10 shown in FIG. 5 would extend laterally from one outer edge 52 of the tissue 51 to the other outer edge 52 of the tissue 51.

I claim:

1. A catamenial device comprising a liquid permeable layer having a first body-facing surface and a second opposed surface, an absorbent body disposed adjacent the opposed surface, said absorbent body comprising a water insoluble particulate hydrogel material at a weight concentration of at least 5 $g/m^2$ of the plan area of the absorbent body, said particulate hydrogel material being disposed between two layers of nonwoven fabric, a liquid impermeable barrier layer disposed on the surface of said absorbent body remote from said liquid permeable layer, and adhesive attachment means for securing said device to a garment, said attachment means being disposed on the surface of said device opposed to said first body facing surface of said liquid permeable layer, wherein the water insoluble particulate hydrogel material exerts a pressure of at least 0.38 kPa after 5 minutes and not less than 0.38 kPa after 30 minutes exposure to 56 times its weight of synthetic urine solution, and in that said device incorporating 0.8 g water insoluble particulate hydrogel material retains at least 40 g of sheeps blood after said body-facing surface is exposed to a supply of said sheeps blood for 20 minutes, a pressure of 17 $g/cm^2$ being applied to said surface for 2 minutes following said exposure.

* * * * *